US007914773B2

(12) United States Patent
Derici et al.

(10) Patent No.: US 7,914,773 B2
(45) Date of Patent: Mar. 29, 2011

(54) HAIR CARE COMPOSITION COMPRISING A DENDRITIC MACROMOLECULE

(75) Inventors: Leo Derici, Bebington (GB); Jason Peter Harcup, Bebington (GB); Ezat Khoshdel, Bebington (GB)

(73) Assignee: Conopco, Inc., Englewood Cliffs, NJ (US)

( * ) Notice: Subject to any disclaimer, the term of this patent is extended or adjusted under 35 U.S.C. 154(b) by 814 days.

(21) Appl. No.: 11/660,488

(22) PCT Filed: Jun. 28, 2005

(86) PCT No.: PCT/EP2005/007016
§ 371 (c)(1),
(2), (4) Date: Feb. 16, 2007

(87) PCT Pub. No.: WO2006/018063
PCT Pub. Date: Feb. 23, 2006

(65) Prior Publication Data
US 2008/0038215 A1 Feb. 14, 2008

(30) Foreign Application Priority Data
Aug. 17, 2004 (EP) .................................. 04254919

(51) Int. Cl.
*A61K 8/72* (2006.01)
*A61Q 5/04* (2006.01)
(52) U.S. Cl. .................................. 424/70.12; 424/70.11
(58) Field of Classification Search .................. None
See application file for complete search history.

(56) References Cited

U.S. PATENT DOCUMENTS

| | | | |
|---|---|---|---|
| 3,660,561 A | 5/1972 | Shepherd et al. | |
| 5,418,301 A * | 5/1995 | Hult et al. ...................... | 525/437 |
| 5,449,519 A | 9/1995 | Wolf et al. ...................... | 424/401 |
| 6,036,962 A * | 3/2000 | Muller et al. ................... | 424/401 |
| 6,068,835 A | 5/2000 | Franzke et al. ............. | 424/70.11 |
| 6,217,889 B1 | 4/2001 | Lorenzi | |
| 6,258,896 B1 | 7/2001 | Abuelyaman et al. | |
| 6,284,233 B1 | 9/2001 | Simon et al. ............... | 424/78.03 |
| 6,287,552 B1 | 9/2001 | Tournilhac et al. ........ | 424/78.03 |
| 6,328,981 B1 | 12/2001 | Boussouira et al. .......... | 424/401 |
| 6,372,237 B1 | 4/2002 | Boussouira et al. .......... | 424/401 |
| 6,379,683 B1 | 4/2002 | Simonnet et al. .......... | 424/401 |
| 6,432,423 B1 | 8/2002 | Maignan et al. .............. | 424/401 |
| 6,475,495 B1 | 11/2002 | Maignan et al. .............. | 424/401 |
| 6,582,685 B1 * | 6/2003 | Adams et al. ............. | 424/70.11 |
| 6,667,044 B1 | 12/2003 | Diec | |
| 2003/0055209 A1 | 3/2003 | Wang | |
| 2004/0115155 A1* | 6/2004 | Salvador et al. ........... | 424/70.13 |
| 2004/0161394 A1 | 8/2004 | Mougin et al. ............ | 424/70.11 |
| 2004/0197416 A1 | 10/2004 | Simonnet et al. ............. | 424/490 |
| 2004/0223986 A9 | 11/2004 | Boussouira et al. .......... | 424/401 |
| 2006/0287425 A1 | 12/2006 | Karlsson et al. | |
| 2007/0202071 A1* | 8/2007 | Morvan et al. ............. | 424/70.17 |
| 2007/0274942 A1 | 11/2007 | Moran et al. ............... | 424/70.19 |

FOREIGN PATENT DOCUMENTS

| | | |
|---|---|---|
| EP | 529 883 A1 | 3/1993 |
| EP | 0 815 827 | 1/1998 |
| EP | 0 880 961 | 12/1998 |
| EP | 0 880 962 | 12/1998 |
| EP | 0 884 047 | 12/1998 |
| EP | 0 987 017 | 3/2000 |
| WO | 94/17125 | 8/1994 |
| WO | 95/20939 | 8/1995 |
| WO | 97/14404 | 4/1997 |
| WO | 99/32076 | 7/1999 |
| WO | 99/32540 | 7/1999 |
| WO | 00/37542 | 6/2000 |
| WO | 01/17485 | 3/2001 |
| WO | 02/098377 | 12/2002 |
| WO | 03/013445 | 2/2003 |
| WO | 03/016392 A1 | 2/2003 |
| WO | 2004/060543 | 7/2004 |
| WO | 2005/032498 | 4/2005 |
| WO | 2005/092275 | 10/2005 |

OTHER PUBLICATIONS

Benthem et al. "Synthesis and Characterization of Bis(2-hydroxypropyl) amide-Based Hyperranched Polyesteramides" Macromolecules 2001, 34. 3559-3566.*
Co-pending Application: Applicant: Bjornberg et al., U.S. Appl. No. 11/660,573.
Co-pending Application: Applicant: Derici et al., U.S. Appl. No. 11/660,572.
Notice of Opposition (dated Sep. 25, 2008) by DSM Nutritional Products AG to grant of EP 17778180 (including translation).
Reply by Unilever (dated Mar. 10, 2009) to Opposition of EP 1778180.
PCT International Search Report in a PCT application PCT/EP2005/007017.
European Search Report in an EP application EP 04 25 8033.
Robbins, "*Chemical and Physical Behavior of Human Hair*", 4th Ed., Springer-Verlag NY, Inc., 2002, pp. 460-461.
Goddard et al., "*Evaluation methods for Hair Assemblies*", Principles of Polymer Science and Technology in Cosmetics and Personal Care, 1999, p. 550.
Abstract of WO2005/092275—published Oct. 6, 2005.
van Bethem, "*Synthesis and Characterization of Bis(2-hydroxypropyl) amide-Based Hyperbranched Polyesteramides*", Macromolecules, 2001, vol. 34, pp. 3559-3566. L.H. Sperling, "Introduction to Physical Polymer Science", Third Ed. 2001, pp. 635-638.
Communication from the EP Patent Office dated Mar. 10, 2009 re: Opposition to EP 1778180.
Letter from Patent Proprietor (dated Sep. 28, 2009) re: Opposition to EP 1778180.

* cited by examiner

*Primary Examiner* — Robert A Wax
*Assistant Examiner* — Danah Al-Awadi
(74) *Attorney, Agent, or Firm* — Ronald A. Koatz

(57) ABSTRACT

A cosmetic and personal care composition comprising a hydrophobically functionalised dendritic macromolecule.

7 Claims, No Drawings

HAIR CARE COMPOSITION COMPRISING A DENDRITIC MACROMOLECULE

FIELD OF THE INVENTION

The present invention relates to cosmetic and personal care compositions, in particular the present invention relates to hair care compositions that leave the hair straight, well aligned and with decreased volume.

BACKGROUND AND PRIOR ART

Straight, perfectly aligned, long hair is seen by many people as attractive. The present application discloses formulations for aligning hair, preventing hair frizzing and decreasing the volume of hair.

Certain dendritic polymers have been suggested for use in the context of personal care.

WO 01/17485 discloses the use of dendritic molecules to style hair, leave-in formulations are preferred particularly hair styling compositions such as hairsprays.

WO97/14404 describes personal wash compositions containing an anionic surfactant as a cleaning agent and a cationic dendrimer as a mildness aid. The preferred cationic dendrimers are polyamidoamine (PAMAM) dendrimers prepared by sequential reactions of ethylenediamine and methyl acrylate.

U.S. Pat. No. 5,449,519 relates to keratolytic or anti-acne compositions in which the keratolytic or anti-acne agent (e.g. salicylic acid) is complexed with a starburst dendrimer of the PAMAM type.

EP 0 880 961 and EP 880 962 describe anti-solar preparations for protection of skin and hair containing a hyperbranched or dendrimeric polyamino-polymer such as hyperbranched polyethyleneimine.

EPO 884 047 relates to the use of polyamine polymers, which may be hyperbranched or dendrimeric, as antioxidant agents for cosmetic or dermatological compositions.

WO 99/32076 and WO 99/32540 concern the use of certain specific disulphide-functionalised hyperbranched polymers and dendrimers in cosmetics and pharmaceuticals as thickening or gelling agents or as film-forming agents.

EP 0 815 827 describes cosmetic compositions for treating hair with a cosmetic base containing at least one dendrimer or dendrimer conjugate. These dendrimers are referred to as poly(iminopropane-1,3-diyl) dendrimers with nitrile or amino terminal groups.

SUMMARY OF THE INVENTION

The present invention provides a cosmetic and personal care composition comprising a hydrophobically functionalised dendritic macromolecule.

A method of treating hair by applying the composition described above to hair is also defined.

The invention also relates to the use of a hydrophobically functionalised dendritic macromolecule for aligning the hair and for decreasing the volume of hair.

DETAILED DESCRIPTION

As used herein, the weight average molecular weight (Me) of a polymer is the sum of the number of polymer molecules and the squared sum of the individual polymer molecules' molecular weight, divided by the summation of the number of polymer molecules and the sum of the individual polymer molecules' molecular weight.

As used herein, "water-soluble" refers to any material that is sufficiently soluble in water to form a clear or translucent solution to the naked eye at a concentration of 1.0% or more by weight of the material in water at 25° C.

Dendritic Macromolecule

Dendritic macromolecules are macromolecules with densely branched structures having a large number of end groups. A dendritic polymer includes several layers or generations of repeating units which all contain one or more branch points. Dendritic polymers, including dendrimers and hyperbranched polymers, are prepared by condensation reactions of monomeric units having at least two different types of reactive groups. Dendrimers are highly symmetric, whereas macromolecules designated as hyperbranched may to a certain degree hold an asymmetry, yet maintaining the highly branched treelike structure.

Dendritic macromolecules normally consist of an initiator or nucleus having one or more reactive sites and a number of branching layers and optionally a layer of chain terminating molecules. Continued replication of branching layers normally yields increased branch multiplicity and, where applicable or desired, increased number of terminal groups. The layers are usually called generations and the branches dendrons.

Compositions of the invention comprise a hydrophobically functionalised dendritic macromolecule. Preferred hydrophobic groups are carbon based. $C_4$-$C_{24}$ alkyl or alkenyl groups are preferred hydrophobic groups, more preferred are $C_6$-$C_{22}$ alkyl or alkenyl groups, especially preferred are $C_8$-$C_{16}$ alkyl or alkenyl groups, most preferred are dendritic macromolecule having $C_{10}$-$C_{14}$ alkyl or alkenyl groups. The hydrophobic groups may include linear and branched hydrophobes as well as arylalkyl groups, however it is preferred if the alkyl hydrophobic groups are linear. The hydrophobic groups may be unsaturated groups but are preferably saturated. The hydrophobic groups are sometimes linked to the dendritic macromolecule through linking groups, suitable linking groups include ester or amide groups.

In some instances it is preferred if the dendritic macromolecule is fully or partially hydrophobically functionalised at the periphery and/or the terminal groups of the dendritic macromolecule. (In the context of the present invention the term periphery means the outer layer or edge of the dendritic macromolecule.)

If the dendritic macromolecule is hydrophobically functionalised at the periphery preferably 5 to 95% of the terminal groups are hydrophobically functionalised, more preferably from 10 to 85%, most preferably from 20 to 60%.

In a further embodiment the number of hydrophobic groups can be expressed as a percentage of the potential sites on the dendritic macromolecule available for hydrophobic modification both on the periphery of the molecule and internally within the molecule. Preferably 10 to 90% of these available sites are hydrophobically modified, more preferably 20 to 70% are hydrophobically modified.

It is preferred if the generation number of the polymer is 2 or greater. The maximum generation number is preferably 9 or less, more preferably 7 or less.

Preferred hydrophobically functionalised dendritic macromolecules are built up from polyester units. Suitable macromolecules of this type are disclosed in U.S. Pat. No. 5,418,301 and can be sold under the tradename Perstop.

Other preferred dendritic macromolecules are built up from polyamide units. Suitable macromolecules of this type are disclosed in Macromolecules 2001, 34, 3559-3566 and are sold under the tradename Hybrane.

The level of hydrophobically functionalised dendritic macromolecule is preferably from 0.001 to 10 wt % of the total composition, more preferably the level is from 0.05 to 8 wt %, most preferably from 0.1 to 5 wt %.

A preferred form of adding the dendritic macromolecule to the composition is to add the macromolecule together with any surfactant and/or long chain alcohol.

Product Form

Compositions of the invention are typically "rinse-off" compositions to be applied to the hair and then rinsed away.

Shampoo Composition

Shampoo compositions of the invention are generally aqueous, i.e. they have water or an aqueous solution or a lyotropic liquid crystalline phase as their major component. Suitably, the composition will comprise from 50 to 98%, preferably from 60 to 90% water by weight based on the total weight of the composition.

Anionic Cleansing Surfactant

Shampoo compositions according to the invention will generally comprise one or more anionic cleansing surfactants which are cosmetically acceptable and suitable for topical application to the hair.

Examples of suitable anionic cleansing surfactants are the alkyl sulphates, alkyl ether sulphates, alkaryl sulphonates, alkanoyl isethionates, alkyl succinates, alkyl sulphosuccinates, alkyl ether sulphosuccinates, N-alkyl sarcosinates, alkyl phosphates, alkyl ether phosphates, and alkyl ether carboxylic acids and salts thereof, especially their sodium, magnesium, ammonium and mono-, di- and triethanolamine salts. The alkyl and acyl groups generally contain from 8 to 18, preferably from 10 to 16 carbon atoms and may be unsaturated. The alkyl ether sulphates, alkyl ether sulphosuccinates, alkyl ether phosphates and alkyl ether carboxylic acids and salts thereof may contain from 1 to 20 ethylene oxide or propylene oxide units per molecule.

Typical anionic cleansing surfactants for use in shampoo compositions of the invention include sodium oleyl succinate, ammonium lauryl sulphosuccinate, sodium lauryl sulphate, sodium lauryl ether sulphate, sodium lauryl ether sulphosuccinate, ammonium lauryl sulphate, ammonium lauryl ether sulphate, sodium dodecylbenzene sulphonate, triethanolamine dodecylbenzene sulphonate, sodium cocoyl isethionate, sodium lauryl isethionate, lauryl ether carboxylic acid and sodium N-lauryl sarcosinate.

Preferred anionic cleansing surfactants are sodium lauryl sulphate, sodium lauryl ether sulphate(n)EO, (where n is from 1 to 3), sodium lauryl ether sulphosuccinate(n)EO, (where n is from 1 to 3), ammonium lauryl sulphate, ammonium lauryl ether sulphate(n)EO, (where n is from 1 to 3), sodium cocoyl isethionate and lauryl ether carboxylic acid (n) EO (where n is from 10 to 20).

Mixtures of any of the foregoing anionic cleansing surfactants may also be suitable.

The total amount of anionic cleansing surfactant in shampoo compositions of the invention generally ranges from 0.5 to 45%, preferably from 1.5 to 35%, more preferably from 5 to 20% by total weight anionic cleansing surfactant based on the total weight of the composition.

Further Ingredients

Optionally, a shampoo composition of the invention may contain further ingredients as described below to enhance performance and/or consumer acceptability.

Co-surfactant

The composition can include co-surfactants, to help impart aesthetic, physical or cleansing properties to the composition.

An example of a co-surfactant is a nonionic surfactant, which can be included in an amount ranging from 0.5 to 8%, preferably from 2 to 5% by weight based on the total weight of the composition.

For example, representative nonionic surfactants that can be included in shampoo compositions of the invention include condensation products of aliphatic ($C_8$-$C_{18}$) primary or secondary linear or branched chain alcohols or phenols with alkylene oxides, usually ethylene oxide and generally having from 6 to 30 ethylene oxide groups.

Other representative nonionic surfactants include mono- or di-alkyl alkanolamides. Examples include coco mono- or di-ethanolamide and coco mono-isopropanolamide.

Further nonionic surfactants which can be included in shampoo compositions of the invention are the alkyl polyglycosides (APGs). Typically, the APG is one which comprises an alkyl group connected (optionally via a bridging group) to a block of one or more glycosyl groups. Preferred APGs are defined by the following formula:

$$RO\text{-}(G)_n$$

wherein R is a branched or straight chain alkyl group which may be saturated or unsaturated and G is a saccharide group. n, may have a value of from about 1 to about 10 or more. materials identified as: Oramix NS10 ex Seppic; Plantaren 1200 and Plantaren 2000 ex Henkel.

A preferred example of a co-surfactant is an amphoteric or zwitterionic surfactant, which can be included in an amount ranging from 0.5 to about 8%, preferably from 1 to 4% by weight based on the total weight of the composition.

Examples of amphoteric or zwitterionic surfactants include alkyl amine oxides, alkyl betaines, alkyl amidopropyl betaines, alkyl sulphobetaines (sultaines), alkyl glycinates, alkyl carboxyglycinates, alkyl amphoacetates, alkyl amphopropionates, alkylamphoglycinates, alkyl amidopropyl hydroxysultaines, acyl taurates and acyl glutamates, wherein the alkyl and acyl groups have from 8 to 19 carbon atoms. Typical amphoteric and zwitterionic surfactants for use in shampoos of the invention include lauryl amine oxide, cocodimethyl sulphopropyl betaine, lauryl betaine, cocamidopropyl betaine and sodium cocoamphoacetate.

A particularly preferred amphoteric or zwitterionic surfactant is cocamidopropyl betaine.

Mixtures of any of the foregoing amphoteric or zwitterionic surfactants may also be suitable. Preferred mixtures are those of cocamidopropyl betaine with further amphoteric or zwitterionic surfactants as described above. A preferred further amphoteric or zwitterionic surfactant is sodium cocoamphoacetate.

The total amount of surfactant (including any co-surfactant, and/or any emulsifier) in a shampoo composition of the invention is generally from 1 to 50%, preferably from 2 to 40%, more preferably from 10 to 25% by total weight surfactant based on the total weight of the composition.

Cationic Polymers

Cationic polymers are preferred ingredients in a shampoo composition of the invention for enhancing conditioning performance.

Suitable cationic polymers may be homopolymers which are cationically substituted or may be formed from two or more types of monomers. The weight average ($M_w$) molecular weight of the polymers will generally be between 100 000 and 2 million daltons.

Suitable cationic polymers include, for example, copolymers of vinyl monomers having cationic amine or quaternary ammonium functionalities with water soluble spacer monomers such as (meth)acrylamide, alkyl and dialkyl (meth)acrylamides, alkyl(meth)acrylate, vinyl caprolactone and vinyl pyrrolidine. The alkyl and dialkyl substituted monomers preferably have C1-C7 alkyl groups, more preferably C1-3 alkyl groups. Other suitable spacers include vinyl esters, vinyl alcohol, maleic anhydride, propylene glycol and ethylene glycol.

Cationic amines can be primary, secondary or tertiary amines, depending upon the particular species and the pH of the composition. In general secondary and tertiary amines, especially tertiary, are preferred.

Amine substituted vinyl monomers and amines can be polymerised in the amine form and then converted to ammonium by quaternization.

The cationic polymers can comprise mixtures of monomer units derived from amine- and/or quaternary ammonium-substituted monomer and/or compatible spacer monomers.

Suitable cationic polymers include, for example:
cationic diallyl quaternary ammonium-containing polymers including, for example, dimethyldiallylammonium chloride homopolymer and copolymers of acrylamide and dimethyldiallylammonium chloride, referred to in the industry (CTFA) as Polyquaternium 6 and Polyquaternium 7, respectively;
mineral acid salts of amino-alkyl esters of homo- and co-polymers of unsaturated carboxylic acids having from 3 to 5 carbon atoms, (as described in U.S. Pat. No. 4,009,256);
cationic polyacrylamides (as described in WO95/22311).

Other cationic polymers that can be used include cationic polysaccharide polymers, such as cationic cellulose derivatives, cationic starch derivatives, and cationic guar gum derivatives.

Cationic polysaccharide polymers suitable for use in compositions of the invention include monomers of the formula:

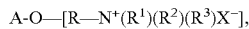

wherein: A is an anhydroglucose residual group, such as a starch or cellulose anhydroglucose residual. R is an alkylene, oxyalkylene, polyoxyalkylene, or hydroxyalkylene group, or combination thereof. $R^1$, $R^2$ and $R^3$ independently represent alkyl, aryl, alkylaryl, arylalkyl, alkoxyalkyl, or alkoxyaryl groups, each group containing up to about 18 carbon atoms. The total number of carbon atoms for each cationic moiety (i.e., the sum of carbon atoms in $R^1$, $R^2$ and $R^3$) is preferably about 20 or less, and X is an anionic counterion.

Another type of cationic cellulose includes the polymeric quaternary ammonium salts of hydroxyethyl cellulose reacted with lauryl dimethyl ammonium-substituted epoxide, referred to in the industry (CTFA) as Polyquaternium 24. These materials are available from the Amerchol Corporation, for instance under the tradename Polymer LM-200.

Other suitable cationic polysaccharide polymers include quaternary nitrogen-containing cellulose ethers (e.g. as described in U.S. Pat. No. 3,962,418), and copolymers of etherified cellulose and starch (e.g. as described in U.S. Pat. No. 3,958,581).

A particularly suitable type of cationic polysaccharide polymer that can be used is a cationic guar gum derivative, such as guar hydroxypropyltrimethylammonium chloride (commercially available from Rhodia in their JAGUAR trademark series). Examples of such materials are JAGUAR C13S, JAGUAR C14, JAGUAR C15, JAGUAR C17 and JAGUAR C16 Jaguar CHT and JAGUAR C162.

Mixtures of any of the above cationic polymers may be used.

Cationic polymer will generally be present in a shampoo composition of the invention at levels of from 0.01 to 5%, preferably from 0.05 to 1%, more preferably from 0.08 to 0.5% by total weight of cationic polymer based on the total weight of the composition.

Suspending Agent

Preferably an aqueous shampoo composition of the invention further comprises a suspending agent. Suitable suspending agents are selected from polyacrylic acids, cross-linked polymers of acrylic acid, copolymers of acrylic acid with a hydrophobic monomer, copolymers of carboxylic acid-containing monomers and acrylic esters, cross-linked copolymers of acrylic acid and acrylate esters, heteropolysaccharide gums and crystalline long chain acyl derivatives. The long chain acyl derivative is desirably selected from ethylene glycol stearate, alkanolamides of fatty acids having from 16 to 22 carbon atoms and mixtures thereof. Ethylene glycol distearate and polyethylene glycol 3 distearate are preferred long chain acyl derivatives, since these impart pearlescence to the composition. Polyacrylic acid is available commercially as Carbopol 420, Carbopol 488 or Carbopol 493. Polymers of acrylic acid cross-linked with a polyfunctional agent may also be used; they are available commercially as Carbopol 910, Carbopol 934, Carbopol 941 and Carbopol 980. An example of a suitable copolymer of a carboxylic acid containing monomer and acrylic acid esters is Carbopol 1342. All Carbopol™ materials are available from Goodrich.

Suitable cross-linked polymers of acrylic acid and acrylate esters are Pemulen TR1 or Pemulen TR2. A suitable heteropolysaccharide gum is xanthan gum, for example that available as Kelzan mu.

Mixtures of any of the above suspending agents may be used. Preferred is a mixture of cross-linked polymer of acrylic acid and crystalline long chain acyl derivative.

Suspending agent will generally be present in a shampoo composition of the invention at levels of from 0.1 to 10%, preferably from 0.5 to 6%, more preferably from 0.9 to 4% by total weight of suspending agent based on the total weight of the composition.

Conditioner Compositions

Another preferred product form for compositions in accordance with the invention is a conditioner for the treatment of hair (typically after shampooing) and subsequent rinsing.

Such conditioner compositions will typically comprise one or more conditioning surfactants, which are cosmetically acceptable and suitable for topical application to the hair.

Suitable conditioning surfactants include those selected from cationic surfactants, used singly or in admixture. Preferably, the cationic surfactants have the formula $N^+R^1R^2R^3R^4$ wherein $R^1$, $R^2$, $R^3$ and $R^4$ are independently ($C_1$ to $C_{30}$) alkyl or benzyl. Preferably, one, two or three of $R^1$, $R^2$, $R^3$ and $R^4$ are independently ($C_4$ to $C_{30}$) alkyl and the other $R^1$, $R^2$, $R^3$ and $R^4$ group or groups are ($C_1$-$C_6$) alkyl or benzyl. More preferably, one or two of $R^1$, $R^2$, $R^3$ and $R^4$ are independently ($C_6$ to $C_{30}$) alkyl and the other $R^1$, $R^2$, $R^3$ and $R^4$ groups are ($C_1$-$C_6$) alkyl or benzyl groups. Optionally, the alkyl groups may comprise one or more ester (—OCO— or —COO—) and/or ether (—O—) linkages within the alkyl chain. Alkyl groups may optionally be substituted with one or more hydroxyl groups. Alkyl groups may be straight chain or branched and, for alkyl groups having 3 or more carbon atoms, cyclic. The alkyl groups may be saturated or may contain one or more carbon-carbon double bonds (eg, oleyl). Alkyl groups are optionally ethoxylated on the alkyl chain with one or more ethyleneoxy groups.

Suitable cationic surfactants for use in conditioner compositions according to the invention include cetyltrimethylammonium chloride, behenyltrimethylammonium chloride, cetylpyridinium chloride, tetramethylammonium chloride, tetraethylammonium chloride, octyltrimethylammonium chloride, dodecyltrimethylammonium chloride, hexadecyltrimethylammonium chloride, octyldimethylbenzylammonium chloride, decyldimethylbenzylammonium chloride, stearyldimethylbenzylammonium chloride, didodecyldimethylammonium chloride, dioctadecyldimethylammonium chloride, tallowtrimethylammonium chloride, dihydrogenated tallow dimethyl ammonium chloride (eg, Arquad 2HT/75 from Akzo Nobel), cocotrimethylammonium chloride, PEG-2-oleammonium chloride and the corresponding hydroxides thereof. Further suitable cationic surfactants include those materials having the CTFA designations Quaternium-5, Quaternium-31 and Quaternium-18. Mixtures of any of the foregoing materials may also be suitable. A particularly useful cationic surfactant for use in conditioners according to the invention is cetyltrimethylammonium chloride, available commercially, for example as GENAMIN CTAC, ex Hoechst Celanese. Another particularly useful cationic surfactant for use in conditioners according to the invention is behenyltrimethylammonium chloride, available commercially, for example as GENAMIN KDMP, ex Clariant.

Another example of a class of suitable cationic surfactants for use in the invention, either alone or together with one or more other cationic surfactants, is a combination of an amidoamine and an acid.

Preferred amidoamines useful herein include stearamidopropyldimethylamine, stearamidopropyldiethylamine, stearamidoethyldiethylamine, stearamidoethyldimethylamine, palmitamidopropyldimethylamine, palmitamidopropyl-diethylamine, palmitamidoethyldiethylamine, palmitamidoethyldimethylamine, behenamidopropyldimethylamine, behenamidopropyldiethylmine, behenamidoethyldiethylamine, behenamidoethyldimethylamine, arachidamidopropyldimethylamine, arachidamidopropyldiethylamine, arachidamidoethyldiethylamine, arachidamidoethyldimethylamine, and mixtures thereof.

Particularly preferred amidoamines useful herein are stearamidopropyldimethylamine, stearamidoethyldiethylamine, and mixtures thereof.

Acid (ii) may be any organic or mineral acid which is capable of protonating the amidoamine in the hair treatment composition. Suitable acids useful herein include hydrochloric acid, acetic acid, tartaric acid, fumaric acid, lactic acid, malic acid, succinic acid, and mixtures thereof. Preferably, the acid is selected from the group consisting of acetic acid, tartaric acid, hydrochloric acid, fumaric acid, and mixtures thereof.

Suitably, the acid is included in a sufficient amount to protonate all the amidoamine present, i.e. at a level which is at least equimolar to the amount of amidoamine present in the composition.

In conditioners of the invention, the level of cationic surfactant will generally range from 0.01 to 10%, more preferably 0.05 to 7.5%, most preferably 0.1 to 5% by weight of the composition.

Conditioners of the invention will typically also incorporate a fatty alcohol. The combined use of fatty alcohols and cationic surfactants in conditioning compositions is believed to be especially advantageous, because this leads to the formation of a lamellar phase, in which the cationic surfactant is dispersed.

Representative fatty alcohols comprise from 8 to 22 carbon atoms, more preferably 16 to 22. Fatty alcohols are typically compounds containing straight chain alkyl groups. Examples of suitable fatty alcohols include cetyl alcohol, stearyl alcohol and mixtures thereof. The use of these materials is also advantageous in that they contribute to the overall conditioning properties of compositions of the invention.

The level of fatty alcohol in conditioners of the invention will generally range from 0.01 to 10%, preferably from 0.1 to 8%, more preferably from 0.2 to 7%, most preferably from 0.3 to 6% by weight of the composition. The weight ratio of cationic surfactant to fatty alcohol is suitably from 1:1 to 1:10, preferably from 1:1.5 to 1:8, optimally from 1:2 to 1:5. If the weight ratio of cationic surfactant to fatty alcohol is too high, this can lead to eye irritancy from the composition. If it is too low, it can make the hair feel squeaky for some consumers.

Further Conditioning Agents

Compositions of the invention may comprise further conditioning agents to optimise wet and dry conditioning benefits.

Particularly preferred further conditioning agents are silicone emulsions.

Suitable silicone emulsions include those formed from silicones such as polydiorganosiloxanes, in particular polydimethylsiloxanes which have the CTFA designation dimethicone, polydimethyl siloxanes having hydroxyl end groups which have the CTFA designation dimethiconol, and amino-functional polydimethyl siloxanes which have the CTFA designation amodimethicone.

The emulsion droplets may typically have a Sauter mean droplet diameter ($D_{3,2}$) in the composition of the invention ranging from 0.01 to 20 micrometer, more preferably from 0.2 to 10 micrometer.

A suitable method for measuring the Sauter mean droplet diameter ($D_{3,2}$) is by laser light scattering using an instrument such as a Malvern Mastersizer.

Suitable silicone emulsions for use in compositions of the invention are available from suppliers of silicones such as Dow Corning and GE Silicones. The use of such pre-formed silicone emulsions is preferred for ease of processing and control of silicone particle size. Such pre-formed silicone emulsions will typically additionally comprise a suitable emulsifier such as an anionic or nonionic emulsifier, or mixture thereof, and may be prepared by a chemical emulsification process such as emulsion polymerisation, or by mechanical emulsification using a high shear mixer. Pre-formed silicone emulsions having a Sauter mean droplet diameter ($D_{3,2}$) of less than 0.15 micrometers are generally termed microemulsions.

Examples of suitable pre-formed silicone emulsions include emulsions DC2-1766, DC2-1784, DC-1785, DC-1786, DC-1788 and microemulsions DC2-1865 and DC2-1870, all available from Dow Corning. These are all emulsions/microemulsions of dimethiconol. Also suitable are amodimethicone emulsions such as DC939 (from Dow Corning) and SME253 (from GE Silicones).

Also suitable are silicone emulsions in which certain types of surface active block copolymers of a high molecular weight have been blended with the silicone emulsion droplets, as described for example in WO03/094874. In such materials, the silicone emulsion droplets are preferably formed from polydiorganosiloxanes such as those described above. One preferred form of the surface active block copolymer is according to the following formula:

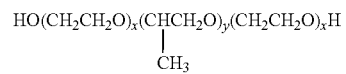

wherein the mean value of x is 4 or more and the mean value of y is 25 or more.

Another preferred form of the surface active block copolymer is according to the following formula:

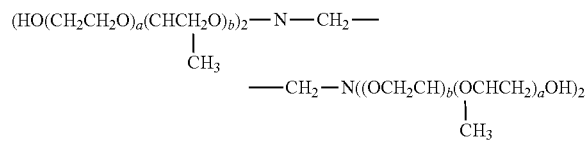

wherein the mean value of a is 2 or more and the mean value of b is 6 or more.

Mixtures of any of the above described silicone emulsions may also be used.

Silicone will generally be present in a composition of the invention at levels of from 0.05 to 10%, preferably 0.05 to 5%, more preferably from 0.5 to 2% by total weight of silicone based on the total weight of the composition.

Other Optional Ingredients

A composition of the invention may contain other ingredients for enhancing performance and/or consumer acceptability. Such ingredients include fragrance, dyes and pigments, pH adjusting agents, pearlescers or opacifiers, viscosity modifiers, preservatives, and natural hair nutrients such as botanicals, fruit extracts, sugar derivatives and amino acids.

The invention is further illustrated with reference to the following, non-limiting examples, in which all percentages are by weight based on total weight unless otherwise specified.

Examples of the invention are illustrated by a number, comparative examples are illustrated by a letter.

EXAMPLES

In-vitro Test Method
Laser Volume Experiment (Switches Treated with Shampoo and/or Conditioner)
Base Wash 2 g/10" European hair switches were base washed using a 14/2 SLES/CAPB solution. 5 switches were grouped together and wetted under running water at 35-40° C. The excess water was removed by running thumb and forefinger along the length of the switch. 1 ml of base was applied along the length of the switch and agitated for 30 seconds. The switch was rinsed under the warm running water for 30 seconds and then a further 1 ml of SLES/CAPB was applied and agitated for another 30 seconds. The switch was given a final rinse for 1 minute.

Shampoo Treatment 5 switches were grouped together and 1 ml of shampoo was placed along the length of the switch. The switch was agitated for 30 seconds, followed by a rinse for 30 seconds. Another 1 ml of shampoo was placed along the length of the switch and agitated for 30 seconds, followed by a rinse for 1 minute. The switches were combed through whilst suspended vertically from a clamp stand, the switch was smoothed by running thumb and forefinger along the length of the switch and then allowed to dry naturally overnight.

Note 5 switches were used per treatment.

Conditioner Treatment 5 switches were grouped together and base washed as above with 14/2 shampoo, then 2 mls of conditioner was placed along the length of the switch and agitated for 1 minute followed by a rinse for 1 minute. The switches were combed through whilst suspended vertically from a clamp stand, the switch was smoothed by running thumb and forefinger along the length of the switch and then allowed to dry naturally overnight.

Laser Measurements

Each switch was suspended vertically from a clamp stand and a 2 mW, $\lambda$=632.8 nm Helium-Neon laser shone perpendicular to the untouched switch approximately 2" from the bottom of the switch. The laser illuminated a cross-section of the switch creating a two dimensional image of white dots on a dark background with each dot representing a single hair fibre. The illuminated image was recorded onto an optical disc using a 35 mm camera.

Analysis

A macro was used to set the discrimination level for each image, (i.e. the threshold value for a clear image resulting in the no. of dots stored onto the disc) and then calculate the x,y co-ordinates of every dot on the image. Another macro in Excel applied a mathematical transformation on all the co-ordinates, to convert the co-ordinates from their apparent position relative to the camera to their actual position in the switch. These actual co-ordinates were used to calculate the mean radial distribution of all the co-ordinates away from the calculated centre, thus providing an indicator for the volume of the switch.

Analysis Results

The volume was normalised with respect to the comparative examples.

Shampoo

Shampoo compositions were prepared according to the formulations of table 1. The dendritic polymer was added to the composition with the surfactant.

TABLE 1

| Chemical name | Weight (as 100% active) |
|---|---|
| Sodium laureth (2 EO) sulphate (SLES) | 14.0 |
| Coco amidopropyl betaine (CAPB) | 2.0 |
| Guar hydroxypropyl trimonium chloride | 0.4 |
| Silicone emulsion | 2.0 |
| dendritic polymer (See table 2) | 2.0 |
| sodium chloride | q.s. |
| water and minors | To 100% |

Shampoo examples were made up using the relevant dendritic macromolecule as detailed in tables 2 and 3. Comparative shampoo example A was made up without a dendritic macromolecule present.

TABLE 2

| Example | Normalised volume |
|---|---|
| 1 | 0.85 |
| 2 | 0.86 |
| A | 1.0 |

Example 1 is the dendritic polymer described in Example 7 of Macromolecules 2001, 34, 3559-3566.

Example 2 is the dendritic polymer described in Example 8 of Macromolecules 2001, 34, 3559-3566

TABLE 3

| Example | Normalised volume |
|---|---|
| 3 | 0.81 |
| A | 1.0 |

Example 3 is Example 31 of U.S. Pat. No. 5,418,301.

Thus the Examples of the invention decreased the volume of the hair.

Conditioner

Conditioner compositions were prepared according to table 4.

TABLE 4

| Chemical name | Weight (as 100% active) |
| --- | --- |
| Cetyl Trimethyl Ammonium Chloride | 0.9 |
| Dioctadecyl Dimethyl Ammonium Chloride | 0.4 |
| Cetearyl alcohol | 4.0 |
| Silicone emulsion | 2.0 |
| dendritic polymer (table 5) | 2.0 |
| Water and minors | To 100% |

Conditioner examples were made up using the relevant dendritic macromolecule as detailed in table 5. Comparative conditioner example B was made up without the dendritic macromolecule present.

TABLE 5

| Example | Normalised volume |
| --- | --- |
| 4 | 0.62 |
| 5 | 0.83 |
| B | 1.00 |

Example 4 is the dendritic polymer described in Example 8 of Macromolecules 2001, 34, 3559-3566

Example 5 is the dendritic polymer described in Example 11 of Macromolecules 2001, 34, 3559-3566

Thus the formulations of the invention decreased the volume of hair

In-vivo Test Data

Salon Workshop

The shampoo formulations were prepared using the formulations in Table 6.

TABLE 6

| Chemical name | Example 5 Weight (as 100% active) | Example C Weight (as 100% active) |
| --- | --- | --- |
| Sodium laureth (2 EO) sulphate (SLES) | 14.0 | 14.0 |
| Coco amidopropyl betaine | 2.0 | 2.0 |
| Guar hydroxypropyl trimonium chloride | 0.4 | 0.4 |
| Silicone emulsion | 2.0 | 2.0 |
| Dendritic polymer | 2.0 | — |
| Sodium chloride | q.s. | q.s. |
| Water and minors | To 100% | To 100% |

The dendritic polymer described in Example 8 of Macromolecules 2001, 34, 3559-3566

Salon Workshop Methodology 2 hairdressers assessed the product (9 panelists for each hairdresser). The shampoo product is applied by applicator as blind test and hairdresser washes panelists accordingly. Each hairdresser assesses and scores the performance of product (pair comparison) and difference scale between 2 products.

TABLE 7

| Attribute | Number of times example 28 chosen | Number of times example C chosen | Significance of win over control |
| --- | --- | --- | --- |
| Good alignment | 16 | 2 | >95% |
| Less fluffy | 16 | 2 | >95% |
| Weighty hair | 16 | 2 | >95% |
| Hair volume | 16 | 2 | >95% |

Overall assessment by hairdressers (n=18)

The invention claimed is:

1. A method of aligning hair and/or decreasing the volume of hair treated with rinse-off hair care compositions relative to treatment with composition without dentritic molecule present which method comprises: applying to the hair a rinse-off hair care composition comprising from 0.1 to 10 wt % of the total composition of a hydrophobically functionalised dendritic macromolecule built up from polyamide units in which the hydrophobically functionalised group of the dendritic macromolecule comprises a $C_4$-$C_{24}$ alkyl or alkenyl group.

2. A method according to claim 1 in which the hydrophobically functionalised group of the dendritic macromolecule comprises a $C_6$-$C_{22}$ alkyl or alkenyl group.

3. A method according to claim 1 in which the hydrophobically functionalised groups of the dendritic macromolecule are situated at the periphery of the macromolecule.

4. A method according to claim 1 in which the hair care composition further comprises a silicone conditioning oil.

5. A method according to claim 1 which further comprises a surfactant.

6. A method as described in claim 1 wherein the rinse-off composition is a shampoo that further comprises from 5 to 20% by weight of anionic cleansing surfactant, based on the total weight of the composition.

7. A method as described in claim 1 wherein the rinse-off composition is a conditioner that further comprises cationic surfactant.

* * * * *